US007375190B2

(12) United States Patent
Cheng et al.

(10) Patent No.: US 7,375,190 B2
(45) Date of Patent: May 20, 2008

(54) RECOMBINANT PROTEIN AND METHOD OF SCREENING FOR AGENTS THAT MODULATE POLYPEPTIDE AGGREGATION

(75) Inventors: Tzu-Hao Cheng, Taipei (TW); Chia-Rung Liu, Yongkang (TW)

(73) Assignee: National Yang-Ming University (TW)

( * ) Notice: Subject to any disclaimer, the term of this patent is extended or adjusted under 35 U.S.C. 154(b) by 0 days.

(21) Appl. No.: 11/523,090

(22) Filed: Sep. 19, 2006

(65) Prior Publication Data

US 2008/0070246 A1 Mar. 20, 2008

(51) Int. Cl.
*C07K 14/00* (2006.01)
*C12N 1/20* (2006.01)
*C12N 15/00* (2006.01)
*C12Q 1/00* (2006.01)

(52) U.S. Cl. .................. 530/350; 435/4; 435/252.3; 435/320.1; 435/975

(58) Field of Classification Search .............. 530/350; 435/4, 252.3, 320.1, 975
See application file for complete search history.

(56) References Cited

OTHER PUBLICATIONS

Brigit E. Riley et al., "Polyglutamine neurodegenerative diseases and regulation of transcription assembling the puzzle," *Genes & Development*, vol. 20, pp. 2183-2192 (2006).
Yoko Kimura et al., "Therapeutic Prospects for the prevention of Neurodegeneration in Huntingdon's Disease and the Polyglutamine Repeat Disorders," *Mini Reviews in Med. Chem.*, vol. 7, pp. 99-106 (2007).
The Huntington's Disease Collaborative Research Group, "A Novel Gene Containing a Trinucleotide Repeat that is Expanded and Unstable on Huntington's Disease Chromosomes," *Cell*, vol. 72, pp. 971-983 (1993).
C.A. Ross, "Polyglutamine Pathogenesis: Emergence of Unifying Mechanisms for Huntingdon's Disease and Related Disorders," *Neuron*, vol. 35, pp. 819-822 (2002).
H.Y. Zoghbi et al., "Glutamien Repeats and Neurodegeneration," *Annu. Rev. Neurosci*, vol. 23, pp. 217-247 (2000).
S.W. Davies et al., "Formation of Neuronal Intranuclear Inclusion Underlies the Neurological Dysfunction in Mice Transgenic for the HD Mutation," *Cell*, vol. 90, pp. 537-548 (Aug. 8, 1997).
M. DiFiglia et al., "Aggregation of Huntingtin in Neuronal Intranuclear Inclusions and Dystrophic Neurites in Brain," *Science*, vol. 277 1990-1993 (Sep. 26, 1997).
L. Mangiarini et al., "Exon 1 of the *HD* Gene with an Expanded CAG Repeat is Sufficient to Cause a Progressive Neurological Phenotype in Transgenic Mice," *Cell*, vol. 87, pp. 493-506 (Nov. 1, 1996).
P. Hemachandra Reddy et al., "Recent advances in understanding the pathogenesis of Huntington's disease," *TINS*, vol. 22, No. 6, pp. 248-255 (1999).
I. Sanchez et al., "Pivotal role of oligomerization in expanded polyglutamine neurodegenerative disorders," *Letters to Nature*, vol. 421, pp. 373-379 (Jan. 23, 2003).

M. Tanaka et al., "Trehalose alleviates polyglutamine-mediated pathology in a mouse model of Huntingdon's disease," *Nature Medicine*, vol. 10, No. 2, pp. 148-154 (Feb. 2004).
C.A. Ross et al., "Polyglutamine fibrillogenesis: The pathway unfolds," *PNAS*, vol. 100, No. 1, pp. 1-3 (Jan. 7, 2003).
J. K. Cooper et al., "Truncated N-terminal fragments of huntingtin with expanded glutamine repeats form nuclear and cytoplasmic aggregates in cell culture," *Human Molecular Genetics*, vol. 7, No. 5, pp. 783-790 (1998).
Shi-Hua Li et al., "Aggregation of N-terminal huntingtin is dependent on the length of its glutamine repeats," *Human Molecular Genetics*, vol. 7, No. 5, pp. 777-782 (1998).
S. Krobitsch et al., "Aggregation of huntingtin in yeast varies with the length of the polyglutamine expansion and the expression of chaperone proteins," *PNAS*, vol. 97, No. 4, pp. 1589-1594 (Feb. 15, 2000).
A.B. Meriin et al., "Huntingtin toxicity in yeast model depends on polyglutamine aggregation mediated by a prion-like protein $Rnq^1$," *J. Cell Biol.*, vol. 157, No. 6, pp. 997-1005 (2002).
J. Carmichael et al., "Bacterial and yeast chaperones reduce both aggregate formation and cell death in mammalian cell models of Huntington's disease," *PNAS*, Vo.. 97, No. 17, pp. 9701-9705 (Aug. 15, 2000).
P.J. Muchowski et al., "Hsp70 and Hsp40 chaperones can inhibit self-assembly of polyglutamine proteins into amyloid-like fibrils," *PNAS*, vol. 97, No. 14, pp. 7841-7846 (Jul. 5, 2000).
L.Z. Osherovich et al., "Multiple Gln/Asn-Rich Prion Domains Confer Susceptibility to Induction of the Yeast [$PSI^+$] Prion," *Cell*, vol. 106, pp. 183-194 (Jul. 27, 2001).
S.R. Collins et al., "Mechanism of Prion Propagation: Amyloid Growth Occurs by Monomer Addition," *PLoS Biol.*, vol. 2, Issue 10, pp. 1582-1590 (Oct. 2004).
I.L. Derkatch et al., "Effects of Q/N-rich, polyQ, and Non-polyQ amyloids on the de novo formation of the [$PSI^+$] prion in yeast and aggregation of Sup 35 in vitro," *PNAS*, vol. 101, No. 35, pp. 12934-12939 (Aug. 31, 2004).
K.C. Gokhale et al., "Modulation of Prion-dependent Polyglutamine Aggregation and Toxicity by Chaperone Proteins in the Yeast Model," *J. Biol. Chem.*, vol. 280, No. 24, pp. 22809-22818 (Jun. 17, 2005).
V. Berthelier et al., "A Microtiter Plate Assay for Polyglutamine Aggregate Extension," *Anal. Biochem.*, vol. 295, pp. 227-236 (2001).
E.E. Wanker et al., "Membrane Filter Assay for Detection of Amyloid-like Polyglutamine-Containing Protein Aggregates," *Methods in Enzymology*, vol. 309, pp. 375-386, (1999).

(Continued)

*Primary Examiner*—Mark Navarro
(74) *Attorney, Agent, or Firm*—Harness, Dickey & Pierce, P.L.C.

(57) ABSTRACT

This invention provides recombinant protein comprising formula as follows:

A-B wherein A is polypeptide containing glutamine-rich domain comprising 8-200 glutamine residues and B is color-alteration enzyme modulated by the domain. This invention also provides an expressing vector and a cell produced therefrom. This invention further provides a method and a kit for screening a therapeutic agent for a neurodegenerative disease.

20 Claims, 4 Drawing Sheets

OTHER PUBLICATIONS

S.K. Pollitt et al., "A Rapid Cellular FRET Assay of Polyglutamine Aggregation Identifies a Novel Inhibitor," *Neuron*, vol. 40, pp. 685-694 (Nov. 13, 2003).

X. Zhang et al., "A potent small molecule inhibits polyglutamine aggregation in Huntington's disease neurons and suppresses neurodegeneration in vivo," *PNAS*, vol. 102, No. 3, pp. 892-897 (Jan. 18, 2005).

U. Guldener et al., "A new efficient gene disruption cassette for repeated use in budding yeast," *Nucleic Acids Res.*, vol. 24, No. 13, pp. 2519-2524 (1996).

D. burke et al., "Methods in Yeast Genetics," Cold Spring Harbor Laboratory Course Manual, App. A, pp. 171-175, 2000 ed.

E. Scherzinger et al., "Huntingtin-Encoded Polyglutamine Expansions Form Amyloid-like Protein Aggregates in vitro and In Vivo," *Cell*, vol. 90, pp. 549-558 (Aug. 8, 1997).

RECOMBINANT PROTEIN AND METHOD OF SCREENING FOR AGENTS THAT MODULATE POLYPEPTIDE AGGREGATION

FIELD OF THE INVENTION

This invention relates to a recombinant protein and a method for screening therapeutic agent for a neurodegenerative disease.

DESCRIPTION OF PRIOR ART

Huntington's disease (HD) is a fatal, inherited neurodegenerative disorder that is characterized by disturbances in movement, cognition, and personality. The mutation that causes HD is an abnormal expansion of CAG repeats in a gene encoding the protein huntingtin (The Huntington's Disease Collaborative Research Group, 1993, Cell 72, 971-983). As this type of mutation to be dominant, a person only needs to inherit one copy of the mutated huntingtin gene to develop HD. In people of western European descent, about 1 in 20,000 is born with a gene that causes HD.

Besides HD, expanded CAG repeats, which encode polyglutamine stretch, have also been observed in at least 8 other neurodegenerative disorders with distinct genes (Ross, 2002, Neuron 35, 819-822; Zoghbi and Orr, 2000, Annu Rev Neurosci 23, 217-247). While the affected gene products are unrelated except for polyglutamine tract, the aggregated polyglutamine is a major component of the protein deposits that are found in patients' brains for all of these diseases. Thus, expanded polyglutamine repeats are thought to result in conformational changes in the proteins that lead to misfolding, aggregation, inclusion body formation, and eventually neuronal cell death (Zoghbi and Orr, 2000, Annu Rev Neurosci 23, 217-247). In a variety of HD model systems, including cell and animal models, studies aimed at understanding the correlation between protein aggregates of mutant huntingtin and cellular dysfunctions have provided evidences for the critical roles of aggregate formation in the progression of HD (Davies et al., 1997, Cell 90, 537-548; DiFiglia et al., 1997, Science 277, 1990-1993; Mangiarini et al., 1996, Cell 87, 493-506; Reddy et al., 1999, Trends Neurosci 22, 248-255).

Chemical reagents that inhibit the formation of protein aggregates were shown to enhance survival of cells and ameliorate pathology of HD in a mouse model (Sanchez et al., 2003, Nature 421, 373-379; Tanaka et al., 2004, Nat Med 10, 148-154). These findings highlight the identification of molecules or genes that modulate the formation of insoluble protein aggregates with expanded polyglutamine.

In HD, there is a threshold of repeat length that causes disease (Ross et al., 2003, Proc Natl Acad Sci USA 100, 1-3). Additionally, age of disease onset is strongly correlated with the length of CAG repeats, which is located within the first exon of huntingtin. There are about 8-25 constitutive repeats of CAG nucleotide sequence in normal person. The repeats identified in the patients' of HD are abnormally expanded to 39 or more. With one incidence of more than 100 CAG repeats, the patient dies at the age of 4. Consistent with these clinical observations, experiments with ectopically expressed polyglutamine in mammalian cell culture demonstrated that efficiency of aggregation increases with the length of polyglutamine track, whereas polypeptides with less than 40 glutamine residues fail to aggregate at all (Cooper et al., 1998, Hum Mol Genet 7, 783-790; Li and Li, 1998, Hum Mol Genet 7, 777-782). The phenomena of protein aggregation resulting from expanded polyglutamine have been reported in yeast cells (Krobitsch and Lindquist, 2000, Proc Natl Acad Sci U.S.A. 97, 1589-1594; Meriin et al., 2002, J Cell Biol 157, 997-100). As the formation of the aggregates being a polyglutamine length-dependent process in mammalian cells, only polypeptides with long stretch above threshold value of 39 constitutive glutamine residues form inclusion bodies in yeast. Notably, the aggregates in yeast, worms and mammalian cells can be modulated by Hsp104p, a yeast chaperone involved in thermal tolerance and disaggregation of misfolded proteins (Carmichael et al., 2000, Proc Natl Acad Sci U.S.A. 97, 9701-9705). Elevated levels of Hsp70 chaperons can ameliorate accumulation of the aggregates in a similar fashion between yeast and mammalian cells (Muchowski et al., 2000, Proc Natl Acad Sci U.S.A. 97, 7841-7846). These results implicate that the mechanisms underlying polyglutamine-mediated protein aggregation are evolutionarily conserved among yeast and other eukaryotic cells.

Hsp104p, a chaperone protein that facilitates the resolubilization of aggregated proteins caused by elevated heat, is an essential component for the formation of polyglutamine-mediated protein aggregation in yeast cells. In Hsp104p deficient cells, ectopic expression of the fusion proteins that are composed of green fluorescent protein (GFP) with 103 successive glutamine residues forms diffused pattern of 103Q-GFP fusion protein under fluorescent microscope, indicating the protein is soluble but not in the aggregated form. In contrast, the signal of 103Q-GFP becomes small grains (or flakes) in cells which express the same fusion construct and posses the function of Hsp104 protein. In addition to Hsp104p, yeast prions have been shown to play a critical role for the cellular formation of polyglutamine aggregation. Yeast prions are proteins that fold in a beta-sheet preferred configuration and form self-replicating aggregates. Three distinct prions, including [PIN$^+$], [PSI$^+$], and [URE3], derived form 3 different gene products are found naturally in yeast cells (Osherovich and Weissman, 2001, Cell 106, 183-194). These proteins commonly contain a stretch of Glutamine/Asparagine (Q/N) rich domain and it is believed that the presence of such domain converts the folding of proteins into prion configuration and triggers the oligomerization/polymerization of prion proteins (Collins et al., 2004, PLoS Biology 2, 1582-1590). The interaction between prion proteins and proteins containing long stretch of polyglutamine residues has been demonstrated (Derkatch et al., 2004, PNAS 101, 12934-12939; Gokhale et al., 2005, J Biol Chem 280, 22809-22818) and it is postulated that the oligomerized prion molecule can function as a seed to facilitate the initiation step of polyglutaimine protein aggregation.

Inactivation of Hsp104p by genetic modulation or specific chemical inhibitor prevents the persistence of protein aggregates generated by prion proteins. With 3-5 mM guanidine hydrochloride (GuHCl) that substantially reduces the activity of Hsp104p, yeast cells gradually loss its ability to maintain prion particle and the characteristic of aggregated prion proteins disappears in conjunction with the change of the protein conformation into monomer, soluble form. Additionally, protein aggregation resulting from extended polyglutamine repeats is impaired under the same condition. Thus, cellular Hsp104p is required for two similar types of protein aggregation in yeast cells.

Various approaches have been established to identify direct inhibitors of polyglutamine aggregation in vitro (Berthelier et al., 2001, Anal Biochem 295, 227-236; Tanaka et al., 2004, Nat Med 10, 148-154; Wanker et al., 1999, Meth Enzymol 309, 375-386). In these instances, formation of insoluble aggregates of purified polypeptides with expanded length of polyglutamine stretch serves as readout. However, these methods are limited to molecules that directly modulate the folding and solubility of proteins and can not uncover other potential targets that regulate intracellular protein aggregation. Two high-throughput cell-based systems, using either cultured mammalian cells or yeast cells, have been established to screen chemical compounds that could down-regulate the formation of protein aggregates with expanded polyglutamine stretch (Pollitt et al., 2003, Neuron 40, 685-694; Zhang et al., 2005, PNAS 102, 892-897). In these studies, several novel lead compounds as well as Y-27632, an inhibitor of the Rho-associated kinase p160ROCK, diminished polyglutamine protein aggregation and reduced neurodegeneration in an animal model of polygluatime disease. These results implicate the advantage of cell-based systems in finding the molecules that indirectly modulate protein aggregation through action on regulatory pathways that are not well defined. Furthermore, in principle, the systems could also identify small molecules that directly target polyglutamine proteins. Thus, cell-based systems are more comprehensive and have provided a better chance to identify therapeutic compounds for HD.

Current available method to conduct such cell-based investigation is mediated, at least in part, through visual assays of GFP fluorescence patterns: expression and cellular distribution of GFP fused with amino-terminal fragment of mutant huntingtin is monitored under fluorescent microscope (U.S. Pat. No. 6,420,122; U.S. Appl. No. 2005221272). While the soluble GFP reporter proteins are diffusely distributed, the aggregated GFP with extended polyglutamine form small grains (or flakes) in cells. This method provides the spatial localization of aggregated proteins within cells; however, it is limited to the molecules with excessive size that are able to be assessed optically. Furthermore, preparation of samples is labor intensive and the instrument used in this assessment is cost-consuming. Due to these reasons, identification of novel therapeutic agents that modulate the fate of cellular protein aggregates with expanded polyglutamine is constrained in current cell-based system. Thus, for the purpose of high-throughput screening, a reliable and easy-detectable method is highly desired.

SUMMARY OF THE INVENTION

This invention provides recombinant protein comprising formula as follows:

A-B wherein A is polypeptide containing glutamine-rich domain comprising 8-200 glutamine residues and B is color-alteration enzyme modulated by the domain.

This invention also provides an expressing vector comprising a nucleotide sequence encoding a recombinant protein described above.

This invention also provides a cell which is transformed or transfected with the vector described above.

This invention also provides a method for screening a therapeutic agent for a neurodegenerative disease comprising: (a) providing a cell expressing the recombinant protein of claim 1, wherein the cell expressing the protein containing 8-25 glutamine residues is positive control group, and the cell expressing the protein containing 85-100 glutamine residues is experimental group; (b) contacting a candidate with the experimental group and positive control group; and (c) identifying the candidate as the therapeutic agent by differentiating color alteration between the experimental group and positive control group.

This invention further provides a kit for screening a therapeutic agent for a neurodegenerative disease comprising the recombinant protein described above.

DETAILED DESCRIPTION OF THE INVENTION

Term Definition

A "polypeptide" is any peptide-linked chain of amino acids, regardless of length or post-translational modification.

The term "aggregation" refers to a process whereby polypeptides stably associate with each other to form a multimeric, insoluble complex, which does not disassociate under physiological conditions.

"ADE2" is the ADE2 gene encoding a phosphoribosylaminoimidazole carboxylase that catalyzes the conversion of p-ribosylamino imidazole (AIR) to p-ribosylamino imidazole carboxylate (CAIR) in the adenine biosynthetic pathway. ADE2 deficient cells are blocked in the adenine biosynthetic pathway and accumulate metabolite intermediate AIR in the vacuole; the intermediate after oxidation gives the cell a red color. In the present invention, ADE2 refers to the gene and the color-alteration enzyme phosphoribosylaminoimidazole carboxylase.

The "neurodegenerative disease", as used herein, refers to any condition characterized by the progressive loss of neurons, due to cell death, in the central nervous system of a subject. More specifically, the neurodegenerative disease of this invention is caused by protein aggregation or polypeptide aggregation.

This invention provides recombinant protein comprising formula as follows:

A-B wherein A is polypeptide containing glutamine-rich domain comprising 8-200 glutamine residues and B is color-alteration enzyme modulated by the domain.

In the preferred embodiment, the glutamine-rich domain comprises 25-100 glutamine residues. In the more preferred embodiment, the glutamine-rich domain comprises 85-100 glutamine residues.

In the recombinant protein, the color-alteration enzyme modulates color alteration for reflecting conformational change of the recombinant protein. For example but not limitation, the color-alteration enzyme can be ADE2 or MET15. While the conformation of the recombinant protein alters, such as aggregation, the enzyme modulates the change of color expression. The color expression can be directly reflected in the color of colony and be observed by naked eye. For example but not limitation, the color-alteration enzyme can be ADE2 or MET 15. In the preferred embodiment, the enzyme is ADE2 (phosphoribosyl-aminoimidazole carboxylase). While the recombinant protein has normal conformation, the soluble form, the ADE2 modulates the cell to express white color. Further, while the recombinant protein has abnormal conformation, aggregative form, the function of ADE2 is blocked and the cell is modulated to express red color.

This invention also provides an expressing vector comprising a nucleotide sequence encoding a recombinant protein as described above. The vector further comprises a promoter, which is positioned in the upstream of nucleotide sequences encoding the recombinant protein. In the preferred embodiment, the promoter is Gal promoter. The Gal promoter is used to control the transcription of the expression vector by carbon source.

This invention also provides a cell which is transformed or transfected with the expression vector as described above. The cell is a bacterium, a yeast, a fungus, a mammalian cell, or an insect cell. In the preferred embodiment, the cell is yeast cell.

In this invention, the color of a cell indicates the conformation status of the recombinant protein via ADE2 modulation way. In an embodiment, a cell expresses red color for reflecting aggregation of the recombinant protein. In another embodiment, a cell expresses white color for reflecting non-aggregation of the recombinant protein.

This invention further provides a method for screening a therapeutic agent for a neurodegenerative disease comprising: (a) providing a cell expressing the recombinant protein as described above, wherein the cell expressing the protein containing 8-25 glutamine residues is positive control group, and the cell expressing the protein containing 85-100 glutamine residues is experimental group; (b) contacting a candidate with the experimental group and positive control group; and (c) identifying the candidate as the therapeutic agent by differentiating color alteration between the experimental group and positive control group. The method further comprises a cell expressing the protein containing 85-100 glutamine residues without the candidate treatment is negative control group, wherein the negative control group is used for confirming the color alteration of the experimental group. As described above, the recombinant protein comprises glutamine-rich domain and color-alteration enzyme. In the preferred embodiment, the color-alteration enzyme is phosphoribosyl-aminoimidazole carboxylase (ADE2). In this method, the color alteration is from red or pink to white.

The neurodegenerative disease is caused by protein aggregation or polypeptide aggregation. The aggregation of naturally occurring polypeptides is often associated with these pathological disorders. Examples of naturally occurring polypeptides having propensities to aggregate include polypeptides which contain extended polyglutamine regions. Such polypeptides and their associated disorders are as follows: huntingtin, which is associated with Huntington's disease; atrophin-1, which is associated with dentatorubralpallidoluysian atrophy; ataxin-1, which is associated with spinocerebellar ataxia type 1; ataxin-2, which is associated with spinocerebellar ataxia type-2; ataxin-3, which is associated with spinocerebellar ataxia type-3; alpha 1a-voltage dependent calcium channel, which is associated with spinocerebellar ataxia type-6; ataxin-7, which is associated with spinocerebellar ataxia type-7; and androgen receptor, which is associated with spinobulber muscular atrophy.

Other naturally occurring polypeptides known for their ability to aggregate include the synuclein proteins, namely alpha, beta and gamma synucleins. Synucleins have been implicated in Alzheimer's disease, Parkinson's disease and breast cancer. Other aggregation-disposed polypeptides include: mutant transthyretin, which is associated with familial amyloid polyneuropathies; beta2 microglobulin, aggregation of which causes complications during chronic renal dialysis; beta amyloid protein, which is associated with Alzheimer's disease; immunoglobulin light chain, which is associated with multiple myelomas and various other B-cell proliferations; and prion proteins, which cause spongiform encephalopathies like Creutzfeldt-Jakob disease and kuru in humans.

In a preferred embodiment of this invention, the neurodegenerative disease is Huntington's disease, dentatorubral-pallidoluysian atrophy, spinocerebellar ataxia, spinobulber muscular atrophy, Alzheimer's disease, Parkinson's disease, Creutzfeldt-Jakob disease and kuru. In a more preferred embodiment, the neurodegenerative disease is Huntington's disease.

The method of this invention is for screening therapeutic agent for neurodegenerative diseases. The therapeutic agent can disrupt or decrease the aggregation caused by the polyglutamine of the recombinant protein. Candidate that can be screened in accordance with the invention include polypeptides, peptide mimetics, antibodies, chemicals and monomeric organic compounds, i.e., "small molecules". In particular, certain classes of compounds may be chosen by one skilled in the art based on knowledge of the mechanism of aggregation of particular aggregation-disposed polypeptides.

More specifically, if the candidate can disrupt or decrease the aggregation of the recombinant protein, the enzyme function of ADE2 can normally express. So that the color of the experimental cell treated with the compound should be white comparing with that treated without the candidate should be red.

This invention further provides a kit comprising the recombinant protein as described above for screening therapeutic agent for a neurodegenerative disease.

The neurodegenerative disease is Huntington's disease, dentatoru-bralpallidoluysian atrophy, spinocerebellar ataxia, spinobulber muscular atrophy, Alzheimer's disease, Parkinson's disease, Creutzfeldt-Jakob disease and kuru. In the preferred embodiment, the neurodegenerative disease is Huntington's disease.

The kit of this invention further comprises a cell for transformation or transfection with the recombinant protein. In the preferred embodiment, the cell is yeast cell. The kit of this invention further comprises a buffer or a medium for maintaining the bioactivities of the cell.

EXAMPLE

The examples below are non-limiting and are merely representative of various aspects and features of the present invention.

Example 1

Color-Based Reporter System Construction

Figure 1:
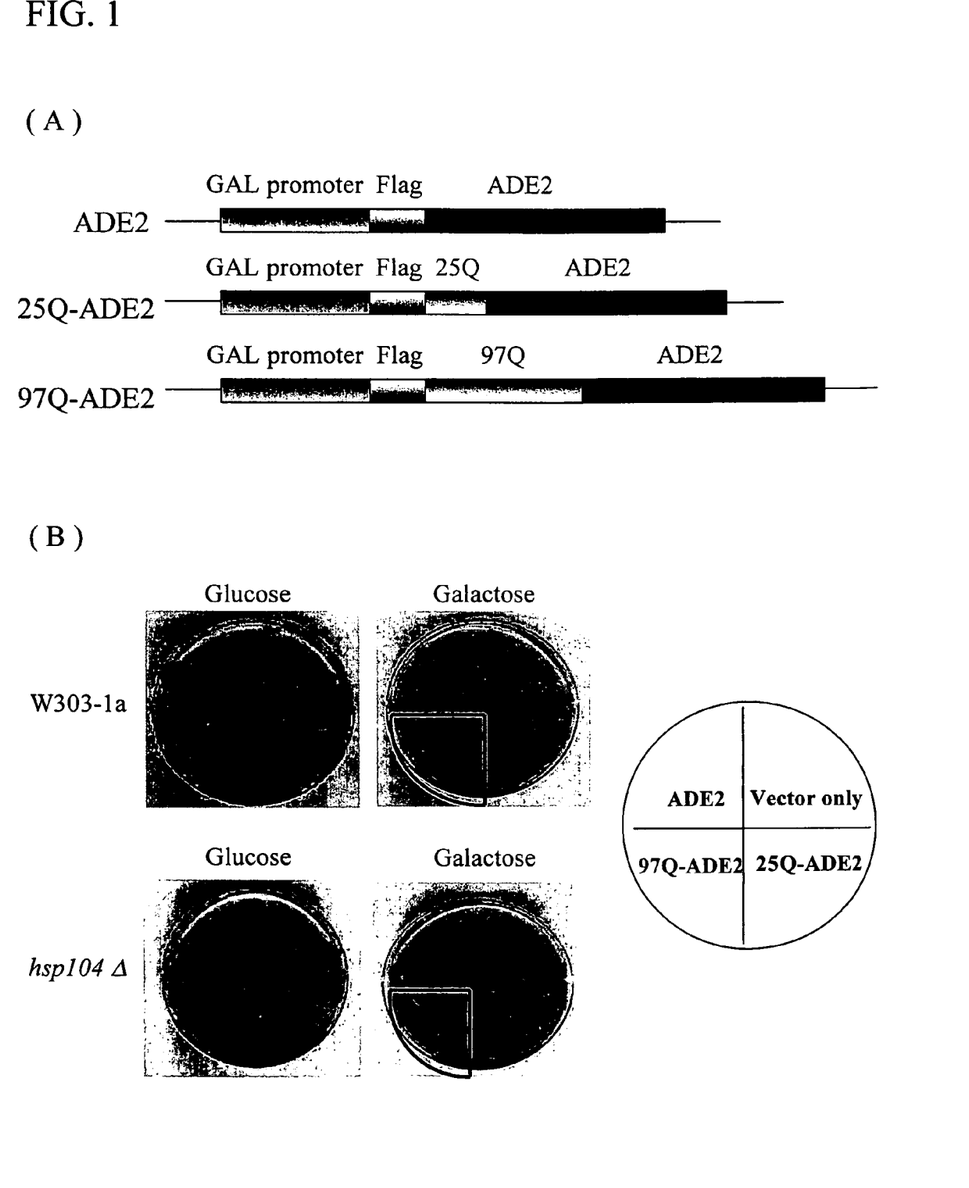
FIG. 1 illustrates (A) the ADE2 expression constructions with different length of polyglutamine residues, and (B) the colony-color phenotypes of cells expressing various ADE2 constructs.

In order to establish a color-based reporter system in which the activity of gene products was dependent on the solubility of the proteins to study the processes of polyglutamine-mediated protein aggregation. Huntingtin's exon1 sequences containing the first 17 amino acids followed by 25 or 97 glutamine residues were fused in frame with ADE2, and a FLAG tag was attached to their amino termini (designated as 25Q-ADE2 and 97Q-ADE2, FIG. 1(A)). The expression of 25Q-ADE2 or 97Q-ADE2 was under the control of Gal1 promoter; thus, the reporter proteins did not express when the cells were cultured in the medium containing glucose until the change of carbon source to galactose. To test whether the constructs created here were able to show a correlation between the length of polyglutamine and colony-color phenotypes, plasmids 25Q-ADE2 or 97Q-ADE2 were transformed into W303-1a yeast strain. As controls, vectors without any inserted DNA or with ADE2 insertion also delivered into the cells by transformation respectively. With ade2-1 mutation, W303-1a cells were defective in biogenesis of adenine and appeared to be dark red color on the adenine low medium (which contained limited but enough amount of adenine for cell growth. However, the cellular phenotype that was associated with accumulation of metabolite intermediate could be visually measured). As lack of expression of the exogenous ADE2 constructs, the color of 4 transformant cells all turned dark red on the adenine low medium containing glucose (FIG. 1(B), left side of top panel). The Cells transformed with constructs expressing ADE2 or 25Q-ADE2 became white color on the medium using galactose as carbon source; however, the cells with 97Q-ADE2 expression constructs remained red color (FIG. 1(B), right side of top panel). Even though the color of 97Q-ADE2 expressing cells was obviously distinct from that of cells expressing ADE2 or 25Q-ADE2, the extent of red color observed in the 97Q-ADE2 expressing cells was not as strong as ADE2 deficient cells (FIG. 1(B), right side of top panel).

Since the colony-color phenotypes of 97Q-ADE2 cells could result from low expression level of the reporter gene, dysfunction of 97Q-ADE2 fusion protein, or other unknown mechanisms, a follow-up genetic experiment was conducted to ascertain the involvement of protein aggregation. Hsp104p, a yeast chaperone protein, was shown to be required for the formation of protein aggregates with extended polyglutamine residues (Krobitsch and Lindquist, 2000, Proc Natl Acad Sci U.S.A. 97, 1589-1594). In W303-1a cells, HSP104 was replaced with an antibiotic selection marker, kanamycin, by one-step gene disruption (Guldener et al., 1996, Nucleic Acid Res 24, 2519-2524). The resultant W303-1a isogenic strain with HSP104 knockout was designated as hsp104Δ. The colony-color phenotypes were assessed as described previously for various ADE2 reporter plasmids in hsp104Δ cells. Whereas the same color patterns retained between W303-1a and hsp104Δ cells that had transfected with empty vector, ADE2, and 25Q-ADE2 respectively, the colony-color of 97Q-ADE2 cells changed from red to white color as the consequence of HSP104 deletion (FIG. 1(B), right side of top panel vs. bottom panel). This result indicated that red colony-color observed in the 97Q-ADE2 expressing cells was dependent on the presence of Hsp104p.

It was of note that the recombinant genes created in this color-based reporter system were expressed from the plasmid vectors that maintain high copy number of plasmid within a single cell. pRS424 as well as pYES2, two high copy vectors with different nutrient selection markers, were tested and showed the expected colony-color phenotype.

Plate preparation for colony-color assay was as following: 6.7 g of yeast nitrogen base lacking amino acids, 20 g of Bacto agar and 1.3 g of drop-out mix that contain amino acids supplement necessary for viable and selective growth of the transformed cells were added to 900 ml of $H_2O$ according to Burke et al. (Burke et al., Methods in Yeast Genetics, 2000 Edition, Gold Spring Harbor Laboratory Press, 171-175). Carbon source, either glucose or galactose, and filter-sterilized adenine were added after autoclaving to final concentrations of 2% and 4 mg/l, respectively. For preparation of media containing guanidine hydrochloride, the chemical reagent was added simultaneously with carbon source and adenine to final concentrations of 1, 3, or 5 μM as indicated. There were about 20 ml of medium in each 10 cm petri dish and 0.2 ml of medium in each well of 48-well microplate.

Example 2

Filter Trap and Slot-Blot Assay

Electron micrographs of insoluble protein aggregates of mutant huntingtin fragments revealed a fibril or ribbon-like morphology, reminiscent of beta-amyloid fibrils in Alzheimer's disease. The fibrils showed a length varied from 100 nm up to several micrometers. Therefore, this unique physical characteristic of the aggregates could be detected biochemically using a filter trap assay in which only proteins with size more than 0.2 micrometers retain on a cellulose acetate membrane (Scherzinger et al., 1997, Cell 90, 549-558). In order to validate the colony-color phenotypes observed in the genetic experiments were caused by the formation of ADE2 protein aggregates, cell lysates were prepared and subjected to filter trap assays.

Figure 2:
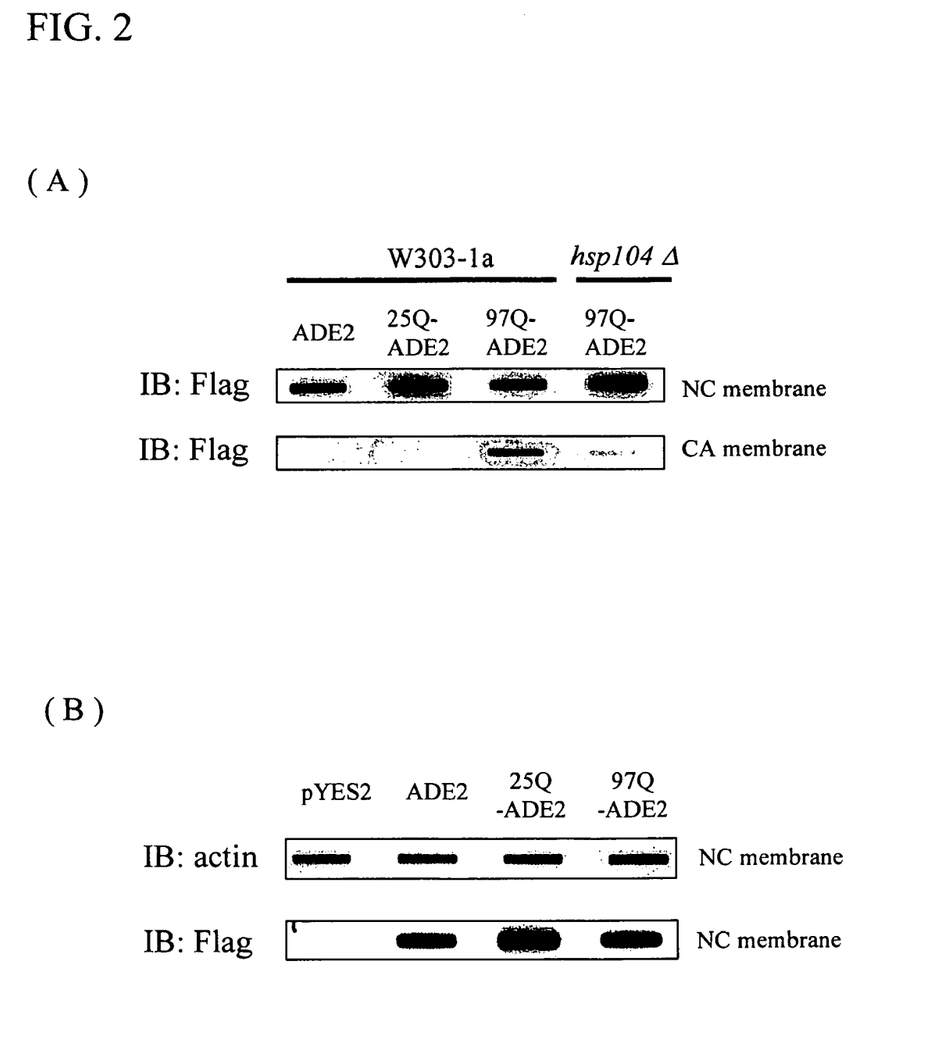
FIG. 2 depicts (A) filter trap assay to detect the insoluble ADE2 aggregates, and (B) similar amounts of ectopic reporter proteins are expressed from the ADE2 constructs by slot-blot assay.

While equal amounts of total proteins were loaded from different ADE2 constructs and strain backgrounds, only 97Q-ADE2 fusion proteins from W303-1a cells were trapped on the cellulose acetate (CA) membrane (FIG. 2(A), bottom panel), indicating the presence of insoluble high molecular weight protein aggregates. As the differential signals detected among these samples in filter trap assay may result from the different expression levels of ADE2 constructs, another biochemical experiment was conducted to examine this possibility. By slot-blot assay in which cell lysates were loaded onto nitrocellulose (NC) membrane and proteins applied were bounded to the membrane without any preference, the levels of the recombinant proteins produced from corresponding ADE2 constructs could be determined by immuno-blotting using monoclonal antibody against Flag epitope. The result showed that comparable amounts of ectopic ADE2 were produced in these cells (FIG. 2(A), top panel). Therefore, the signal detected in the filter trap assay could not be attributed by differential expression of ADE2 constructs and the formation of ADE2 aggregates was dependent on the length of polyglutamine track as well as the presence of Hsp104 protein. With the combination of genetic and biochemical experiments described above, it clearly demonstrated that the novel reporter system developed here indeed was able to reveal the cellular status of recombinant protein solubility by the appearance of cellular color.

In order to further ensure that the amounts of cellular proteins loaded in our biochemical experiments were equivalent and that anti-Flag antibody used was specifically probed to ectopic ADE2 proteins, slot-blot assays were applied to confirm these issues. With equivalent amounts of cell lysates loaded, the protein levels of actin were determined by immuno-blotting and showed no significant difference among theses samples tested (FIG. 2(B), top panel), indicating that similar amounts of cellular proteins were extracted and examined in the slot-blot assay. Actin is a cytoskeleton protein and its protein level is commonly used as an index for loading control. As the recombinant ADE2 proteins created in this investigation all contained a Flag epitope, the presence of ectopic ADE2 could be detected by slot-blot assay using antibody against Flag epitope. While similar extent of signal was observed from cells expressing recombinant ADE2 proteins as indicated by ADE2, 25Q-ADE2, and 97Q-ADE2, there was absence of signal for the one that did not express ectopic protein as indicated by pYES2 (FIG. 2(B), bottom panel). This result showed that the antibody used here does not cross interact with yeast endogenous proteins and it recognizes the ADE2 recombinant proteins specifically.

The experimental procedures for slot-blot assay were following: Nitrocellulose (NC) membrane was pre-wetted with TBS (20 mM Tris, 500 mM NaCl), then assembled into Bio-Dot apparatus (BIO-RAD) in which 3 filter papers (BIO-RAD) were on the bottom as a support and NC membrane was on the top. After assembly of the Bio-Dot apparatus, 200 μl TBS buffer was added into each loading well to rinse the membrane followed by the addition of diluted cell lysate (3 μl prepared cell lysate mixed with 197 μl TBS buffer). When the lysate has completely drained from the apparatus by gravity, 200 μl TBS buffer was loaded again to reduce residual proteins within the loading well. Following the step of TBS wash, 200 μl TTBS (20 mM Tris, 500 mM NaCl, and 0.05% Tween 20) was applied as washing buffer and the solution was sucked out by vacuum pump. The membrane was subjected to TTBS wash twice followed by removal of the membrane from the Bio-Dot apparatus and detection of trapped proteins by Western blotting. The membrane was then incubated with blocking buffer (5% rehydrated nonfat dried milk and 0.2% Triton X-100 in phosphate buffered saline, pH 7.4) and subsequently incubated with the appropriate first antibody (anti-actin, anti-Flag antibodies) and secondary antibody (anti-goat HRP, anti-mouse HRP) for immuno-blotting. The signal for the immuno-blotting was detected by enhanced chemiluminescence (ECL) reagents. For filter trap assay, it follows the same experimental procedure as slot-blot assay, except NC membrane (Schleicher & Schuell, 0.45 μm) was replaced by cellulose acetate (CA) membrane (Schleicher & Schuell, 0.2 μm).

Example 3

Validation For Color-Based System in Drug Screening

Figure 3:
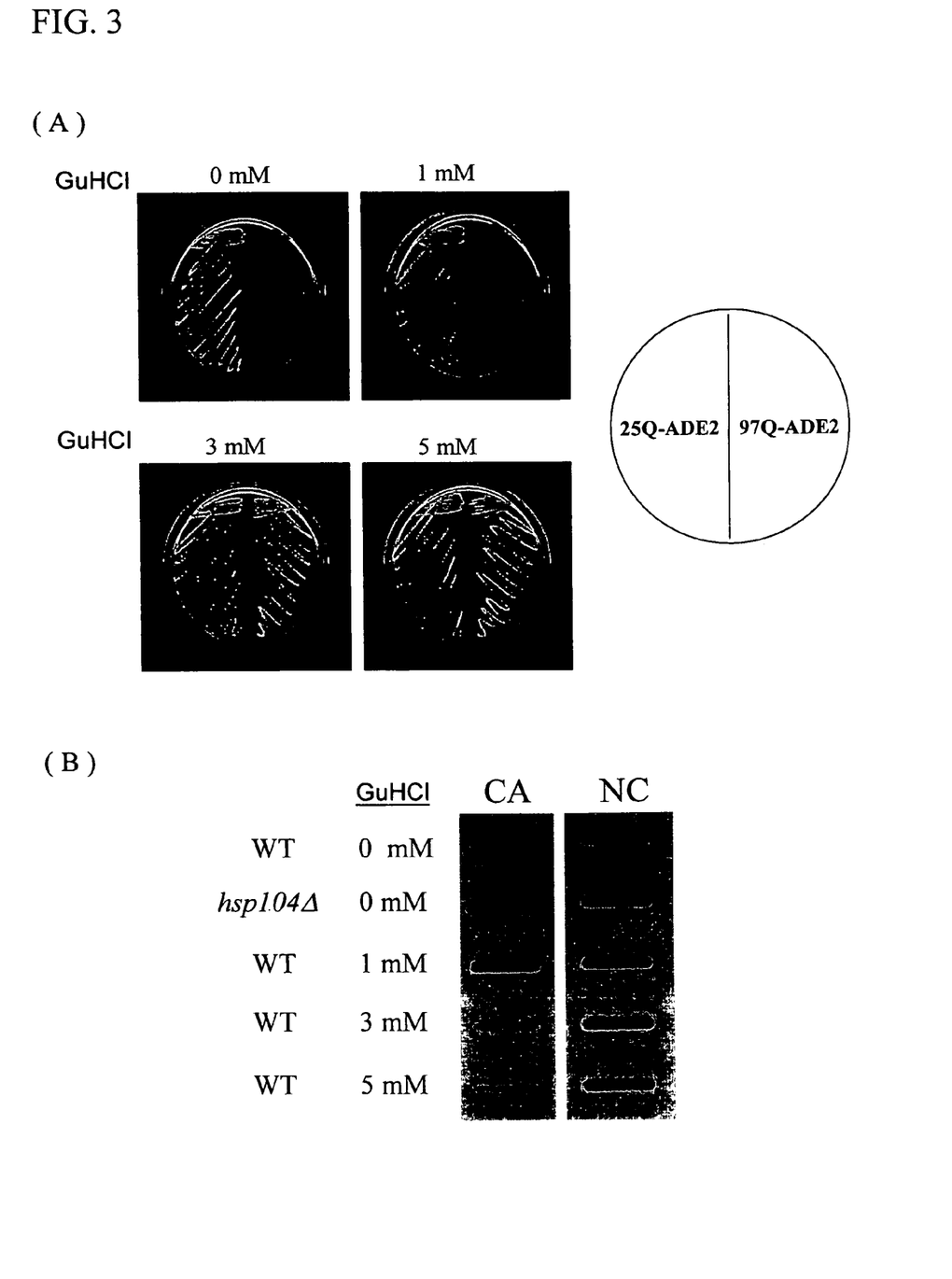
FIG. 3 illustrates (A) validation of the color-based system in drug screening, and (B) the change of cellular color observed in (A) is due to decreased level of 97Q-ADE2 aggregation.

Hsp104p was a member of the Hsp100p families and it could facilitate the solubilization of aggregated proteins caused by heat or stress. It has been known that Hsp104p was also involved in the formation of protein aggregates with expanded polyglutamine stretch in yeast cells. In the absence of Hsp104p function, yeast cells did not show the appearance of polyglutamine protein aggregation, indicating Hsp104p was a necessary component for the genesis of the protein aggregates. The activity of Hsp104p could be modulated by a well-studied chemical inhibitor, guanidine hydrochloride. This chemical reagent, at a concentration of mM, could penetrate into yeast cells and block the ATPase activity of Hsp104p, which was essential for the enzymatic activity of the protein. It was known that yeast cells subjected to guanidine hydrochloride treatment dramatically lost their ability to form polyglutamine protein aggregates through the inhibition of Hsp104p and/or the clearance of prion proteins. Thus, guanidine hydrochloride was used to validate our colony color system that has potential for screening small chemical compounds in preventing the protein aggregation. Cells expressing 25Q-ADE2 or 97Q-ADE2 were grown on adenine low media that contain guanidine hydrochloride at a final concentration of 0, 1, 3 and 5 mM. As 25Q-ADE2 fusion protein did not aggregate, the cells constantly showed colony color of white under the experimental conditions tested (FIG. 3(A), left side of 10-cm Petri dish). In contrast, the cellular color phenotype of cells expressing 97Q-ADE2 changed from red to pink and white as a function of guanidine hydrochloride concentration (FIG. 3(A), right side of Petri dish), suggesting the chemical could inhibit polyglutamine aggregation in a dose dependent manner. At the concentration of 5 mM, the appearance of colony color was indistinguishable between cells expressing 25Q-ADE2 and 97Q-ADE2.

In order to confirm the change of phenotype observed was caused by the alteration of protein solubility, the combination of filter trap and slot blot assays was applied for detecting the level of polyglutamine protein aggregates within these cells. The aggregates of 97Q-ADE2 in wild type and HSP104 deleted cells, designed as WT and hsp104Δ, were served as experimental controls. Analogous to the experimental procedure described in FIG. 2(A), the result revealed that significant amount of the fusion protein was trapped on cellulose acetate (CA) membrane without and with 1 mM guanidine hydrochloride treatment (FIG. 3(B), lane 1 and 3), while little and no signal were detectable for samples prepared from cells continuously treated with guanidine hydrochloride at a final concentration of 3 and 5 mM respectively (FIG. 3(B), lane 4 and 5). Thus, the reduction of polyglutamine protein aggregation caused by Hsp104p inhibitor was tightly associated with the change of cellular phenotype and could be visibly detected by the colony color system.

Example 4

Validation for Color-Based System in Drug Screening

Figure 4:
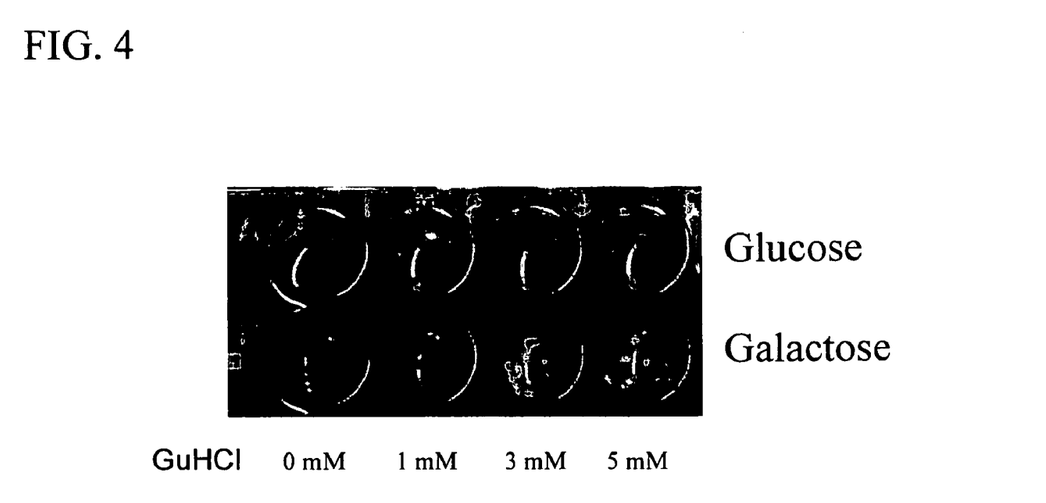
FIG. 4 shows validation of the color-based system in drug screening. The yeast is treated with various concentrations of guanidine hydrochloride (GuHCl) and cultured in 48-well microplate.

For the purpose of drug screening, small volume of medium for examining the colony color phenotype of cells has advantage in saving the amount of candidate compound tested. To this end, the experiment shown in FIG. 3(A) was re-applied in 48-well microplate, instead of 10 cm Petri-dish. With glucose or galactose as carbon source, the transformed cells were grown on adenine low media containing guanidine hydrochloride at a final concentration of 0, 1, 3 and 5 mM as indicated. The phenotype of cells on glucose media could be served as a control to ensure that the treatment of candidate compound would not interfere with the appearance of cellular color, such as the change of colony color from red to white and this might generate false positive result during the drug screening. Consistent with the result shown in FIG. 3(A), 97Q-ADE2 expressing cells changed their cellular colors from red to white upon the treatment of guanidine hydrochloride in a dose dependent manner (FIG. 4, second row). Furthermore, cells that did not express 97Q-ADE2 showed red colony color and the cellular phenotype remained the same under the experimental conditions (FIG. 4, first row), indicating guanidine hydrochloride does not have a negative impact on our color system. Given the above, it demonstrated that a kit for screening candidate compounds that inhibit the formation of polyglutamine protein aggregates.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A recombinant protein comprising formula as follows:

A-B wherein A is polypeptide containing glutamine-rich domain comprising 8-200 glutamine residues and B is color-alteration enzyme modulated by the domain.

2. The recombinant protein of claim 1, wherein the glutamine-rich domain comprises 25-100 glutamine residues.

3. The recombinant protein of claim 1, wherein the enzyme reflects conformation change of the recombinant protein.

4. The recombinant protein of claim 3, wherein the enzyme is phosphoribosylaminoimidazole carboxylase (ADE2).

5. An expressing vector comprising a nucleotide sequence encoding a recombinant protein of claim 1.

6. The vector of claim 5, which further comprises a promoter, which is positioned upstream of nucleotide sequence encoding the recombinant protein.

7. A cell which is transformed or transfected with the vector of claim 5.

8. The cell of claim 7, which is a bacterium, a yeast, a fungus, a mammalian cell, or an insect cell.

9. The cell of claim 7, which expresses red color for reflecting aggregation of the recombinant protein.

10. A method for screening a therapeutic agent for a neurodegenerative disease comprising:
    (a) providing a cell expressing the recombinant protein of claim 1, wherein the cell expressing the protein containing 8-25 glutamine residues is positive control group, and the cell expressing the protein containing 85-100 glutamine residues is experimental group;
    (b) contacting a candidate with the experimental group and positive control group; and
    (c) identifying the candidate as the therapeutic agent by differentiating color alteration between the experimental group and positive control group.

11. The method of claim 10, which further comprises a cell expressing the protein containing 85-100 glutamine residues without the candidate treatment is negative control group.

12. The method of claim 11, wherein the negative control group is used for confirming the color alteration of the experimental group.

13. The method of claim 10, wherein the neurodegenerative disease is caused by protein aggregation or polypeptide aggregation.

14. The method of claim 13, wherein the neurodegenerative disease is Huntington's disease, dentatorubralpallidoluysian atrophy, spinocerebellar ataxia, spinobulber muscular atrophy, Alzheimer's disease, Parkinson's disease, Creutzfeldt-Jakob disease and kuru.

15. The method of claim 10, wherein the recombinant protein containing glutamine-rich domain and phosphoribosylaminoimidazole carboxylase (ADE2).

16. The method of claim 10, wherein the color alteration is from red or pink to white.

17. A kit for screening a therapeutic agent for a neurodegenerative disease comprising the recombinant protein of claim 1.

18. The kit of claim 17, wherein the neurodegenerative disease is Huntington's disease, dentatorubralpallidoluysian atrophy, spinocerebellar ataxia, spinobulber muscular atrophy, Alzheimer's disease, Parkinson's disease, Creutzfeldt-Jakob disease and kuru.

19. The kit of claim 17, which further comprises a cell for transformation or transfection with the recombinant protein.

20. The kit of claim 19, wherein the cell is yeast cell.

* * * * *